US00PP35985P2

(12) United States Plant Patent
Ruter

(10) Patent No.: US PP35,985 P2
(45) Date of Patent: Jul. 9, 2024

(54) ***ILEX* PLANT NAMED 'RUTHOL8'**

(50) Latin Name: ***Ilex* hybrid *(Ilex crenata* x *I. maximowicziana)***
Varietal Denomination: RutHol8

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 18/225,815

(22) Filed: Jul. 25, 2023

(51) Int. Cl.
*A01H 6/00* (2018.01)

(52) U.S. Cl.
USPC ..... Plt./247

(58) Field of Classification Search
USPC ..... Plt./226, 247
See application file for complete search history.

*Primary Examiner* — Susan McCormick Ewoldt
(74) *Attorney, Agent, or Firm* — Thomas | Horstemeyer, LLP

(57) ABSTRACT

A new and distinct cultivar of *Ilex* plant named 'RutHol8' is characterized by a combination of its upright, v-shaped growth habit, its attractive reddish new growth, its intermediate height:width ratio, and its resistance to spider mites.

2 Drawing Sheets

Genus and species: Botanical designation: *Ilex* hybrid (*Ilex crenata* x *I. maximowicziana*).

Variety denomination: The new *Ilex* is of the cultivar denomination 'RutHol8'.

BACKGROUND OF THE INVENTION

The present invention relates to a new and distinct hybrid cultivar of *Ilex* holly plant hereinafter referred to by the cultivar name 'RutHol8'.

The new 'RutHol8' variety is a product of a planned breeding program conducted by the inventor in Watkinsville, GA. The objective of the *Ilex* breeding program is to create new plant cultivars with novel forms of growth, good cold hardiness, and resistance to damage from spider mites, insects and diseases.

The new 'RutHol8' plant is an F2 product of a cross between F1 hybrids of the cross *Ilex crenata* (unpatented, unnamed female) x *I. maximowicziana* (unpatented, unnamed male) plant. The initial cross was made in 2010, and the F1 plants were grown an isolated block. Seed was collected from an open pollinated F1 seedling (female) from the original cross. The collected seed was sown in fall of 2010, and 276 F2 seedlings were taken to Dearing, GA in spring of 2012. 'RutHol8', one of the F2 plants grown from the collected seed, was selected for further evaluation in 2014. 'RutHol8' has been evaluated in container production since 2014. 'RutHol8' has been evaluated through trials at a horticultural farm in the field in Watkinsville, GA since fall of 2015.

Asexual reproduction of the new *Ilex* 'RutHol8' variety was made by vegetative terminal cuttings in a controlled environment in Dearing, GA and Watkinsville, GA and has been continued since 2014. Observations of the new variety and resulting progeny have shown that the unique features of this new *Ilex* cultivar 'RutHol8' are stable and have reproduced true to type in successive generations.

SUMMARY OF THE INVENTION

The cultivar 'RutHol8' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Ilex* x cultivar named 'RutHol8'. In combination, these traits set 'RutHol8' apart from all other existing varieties of *Ilex* known to the inventor.

1. 'RutHol8' exhibits an upright, v-shaped growth habit;
2. 'RutHol8' has a height:width ratio of about: 2:1 to about 2.3:1;
3. 'RutHol8' exhibits attractive reddish new growth; and
4. 'RutHol8' exhibits tolerance of spider mites (*Tetranychus*).

COMPARISON WITH OTHER VARIETIES

Plants of the new *Ilex* 'RutHol8' differ from the most similar *Ilex* cultivars, such as 'RutHol4' (U.S. Plant Pat. No. 32,759), based on at least some of the above characteristics. The new 'RutHol8' is a male plant, while, in contrast, 'RutHol4' is a female plant. 'RutHol8' has an ascending, v-shaped habit whereas 'RutHol4' has a dense, conical habit. In one growing trial, five-year-old (from cutting) 'RutHol8' plants growing in the ground averaged about 96 in high, while comparable 'RutHol4' plants averaged about 84 in high. The height-to—width ratio of 'RutHol4' is less than the height-to-width ratio of 'RutHol8'. In comparison, the 'RutHol4' variety had a height-to-width ratio of about 1.3:1, while 'RutHol8' has a height-to-width ratio of about 2:1-2.3:1. Also, the leaves of the 'RutHol8' plant are wider than the leaves of 'RutHol4'. The leaves of the 'RutHol8' are typically from about 25 to 40 mm long and 15 to 20 mm wide with an acute apex. In comparison, the leaves of 'RutHol4' are typically 30 to 40 mm long and 10 to 15 mm wide with an acuminate apex. Emerging leaves of 'RutHol8' are Greyed Purple 183B (R.H.S.) and mature leaves are Green 136A (R.H.S.). In comparison, emerging leaves of 'RutHol4' are Greyed Orange 165A (R.H.S.) and mature leaves are Green 137A (R.H.S.).

All of the F1 male and female plants from the original *I. crenata* x *I. maximowicziana* cross were destroyed. Therefore, a direct comparison cannot be made between 'RutHol8' and the F1 parent plants.

BRIEF DESCRIPTION OF THE FIGURES

The accompanying colored photographic illustrations show the overall appearance and distinct characteristics of the new cultivar of 'RutHol8' showing the colors as true as possible with the photographic and printing technology utilized. Colors in the photographs may differ slightly from the color values cited in the detailed botanical description. The photographs were taken of 7-year-old plants grown outdoors in Watkinsville, Georgia in March of 2022 and are described in the captions below.

The photograph labeled

The photograph labeled

DETAILED BOTANICAL DESCRIPTION

Figure 1:
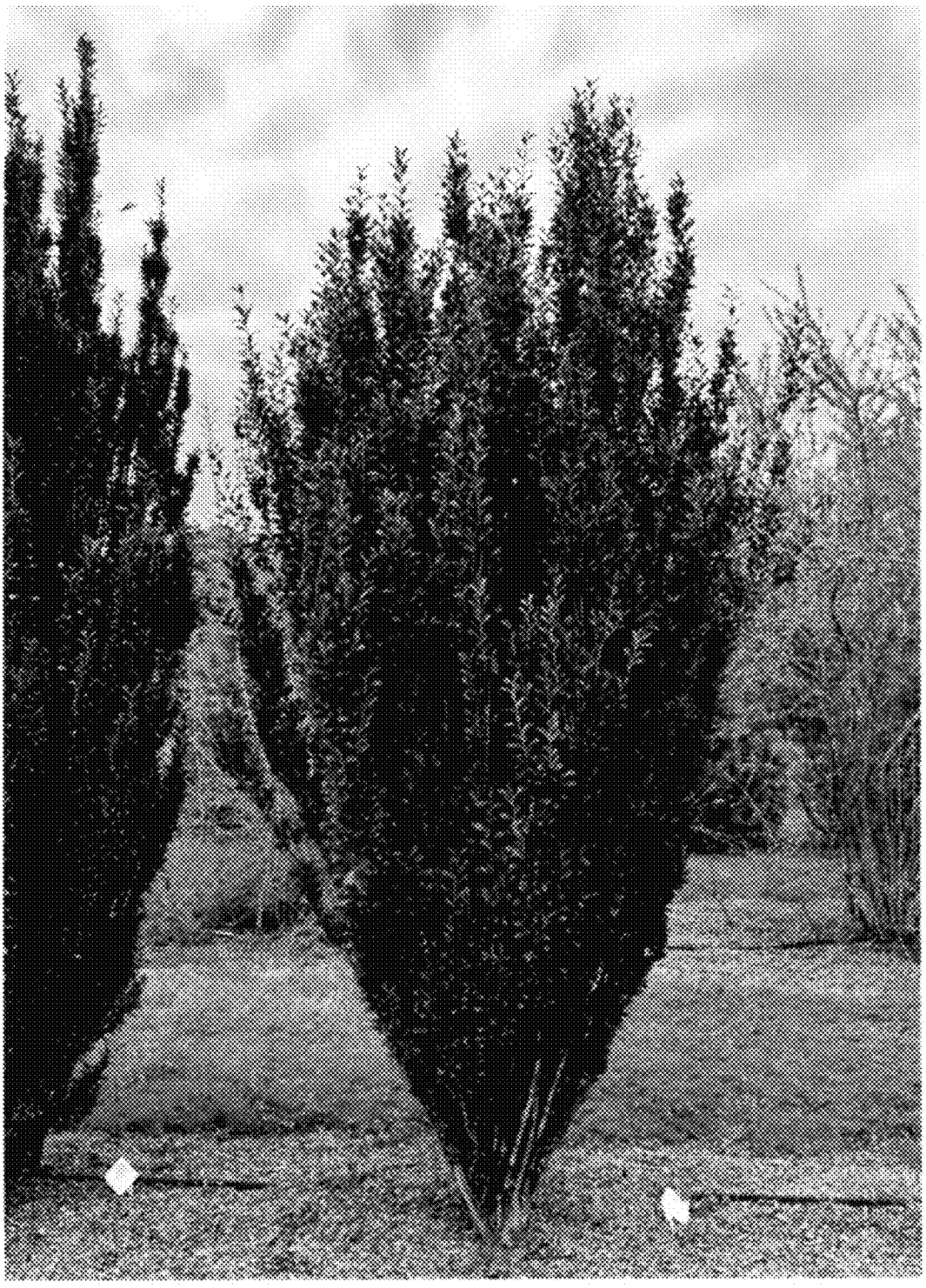
FIG. 1 is a photograph of a 'RutHol8' plant and depicts the overall plant habit of 'RutHol8' with the upright, v-shaped habit.
Figure 2:
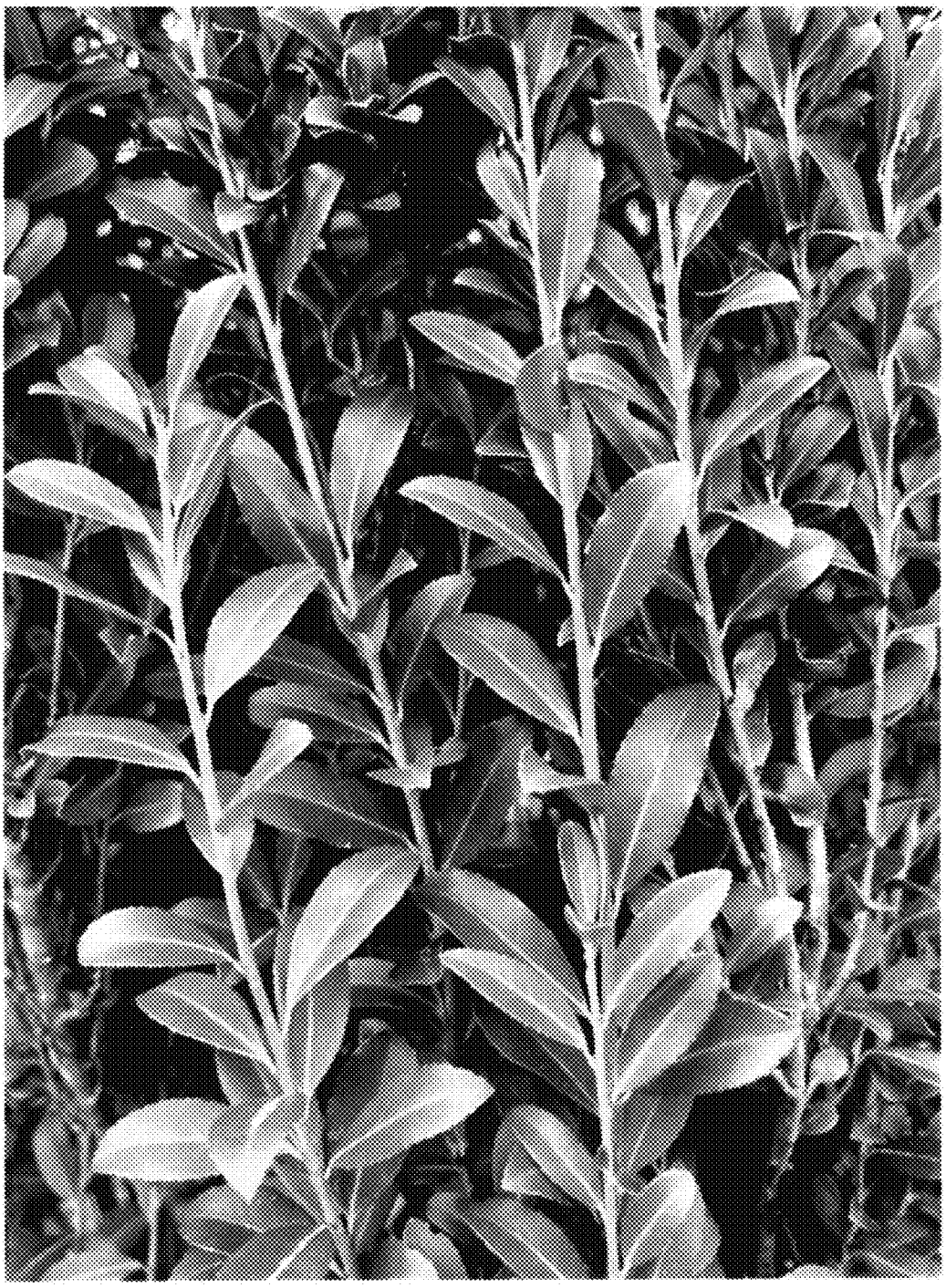
FIG. 2 depicts a close-up view of foliage of the 'RutHol8' plant of FIG. 1.

The following traits have been consistently observed in the original plants of the new 'RutHol8' and in asexually propagated progeny grown in Watkinsville, Georgia, and, to the best knowledge of the inventors, their combination forms the unique characteristics of the new variety *Ilex* 'RutHol8'. The following is a detailed description of the *Ilex* x cultivar named 'RutHol8'. Data was collected from plants growing in a horticultural farm at Watkinsville, GA from 5-year-old plants. The average temperatures ranged from extreme lows of about 20° F. to 30° F. in the winter, and extreme highs of about 90° F. to 100° F. in summer.

Throughout this specification, color names beginning with a small letter signify that the name of that color, as used in common speech, is aptly descriptive. Color names beginning with a capital letter designate values based upon The R.H.S. Colour Chart, 6$^{th}$ edition published in 2015 by The Royal Horticultural Society (R.H.S.), London, England.

Parentage: Female parent—*Ilex crenata* x *Ilex maximowicziana* (female, F1); male parent—*Ilex crenata* x *Ilex maximowicziana* (male, F1).

Growth and propagation: Propagation type—vegetative terminal cuttings; growth rate—moderate; root description—typically about 4-8 roots arising from the base of the cuttings; rooting habit—moderate.

Plant description

*Habit*.—Upright, v-shaped shrub.

*Usage*.—Various uses, including landscaping, ornamental, container, border, hedge, and mass planting.

*Vigor*.—Moderate to vigorous.

*Size of plant*.—5 years in field. A. Height: From soil level to top of plant, about 96 in. B. Width: About 42 in. C. Ratio (h:w): About 2:1-2.3:1.

*Stem*.—Medium strength. A. Color (R.H.S.): Yellow-Green 144A. B. Length: About 3-25 mm. C. Diameter: About 2-2.5 mm. D. Texture/pubescence: Moderately hispid on new growth. E. Shape: 4-sided. F. Odor (of bruised stem): None detected. G. Internode length: About 18-25 mm. H. Shoot angle: About 75-85 degrees. I. Quantity: Numerous, with an average of about 25 main branches and about 10 lateral branches per main branch. J. Lenticles: Absent.

*Branch*.—A. Color (R.H.S.): Yellow-Green 144A. B. Length: About 1.8-2.2 m. C. Diameter: About 2-2.5 cm. D. Texture/pubescence: Moderately hispid on new growth.

*Leaf*.—A. Color (R.H.S.): 1. Upper leaf surface: Emerging leaves Greyed Purple 183B, mature leaves Green 136A. 2. Lower leaf surface: Emerging and mature — Green 138A, sunken stoma. B. Mature size (L×W): About 25-40 mm×15-20 mm; Type — simple. C. Apex: Acute. D. Base: Cuneate. E. Margin: Serrulate. F. Shape: Elliptical. G. Lobes: Absent. H. Pubescence: None. I. Arrangement on stem: Alternate. J. Venation: Pinnate, same color as leaf. K. Texture: Leathery (both upper and lower surfaces). L. Leaf angle: About 45-65 degrees. M. Odor when crushed: None detected. N. Leaf number: Average of about 2 per cm/stem.

*Petiole*.—A. Length: About 5 mm. B. Shape: Oval. C. Color (R.H.S.): Green 138A. D. Texture/pubescence: Moderately hispid. E. Diameter: About 1.5 mm.

*Flower*.—A. Number/inflorescence: B. Axillary or terminal: Axillary. C. Symmetry: Regular. D. Attitude: Erect. E. Fragrance: None detected. F. Petals. 1. Quantity: About 4. 2. Size (L×W): About 3 mm×3 mm. 3. Shape Ovate. 4. Apex Round. 5. Base Truncate. 6. Margin Smooth, entire. 7. Color at peak of bloom Yellow-Green 145C. 8. Texture/pubescence Smooth, none. 9. Arrangement Regular. G. Pedicels 1. Color Yellow Green 144A. 2. Pubescence Sporadic pubescent. 3. Length About 5-7 mm. 4. Aspect Wrect. 5. Strength Strong. H. Sepals 1. Number About 4. 2. Size (L×W) About 1×1.5 mm. 3. Shape Acuminate. 4. Pubescence <0.5 mm, hyaline. 5. Color Yellow Green 144A. 6. Apex Acute. 7. Base Rounded. I. Stamens: 1. Number: 4. 2. Anther: a) Size (L×W): About 0.5 mm×0.5 mm. b) Shape: Oval. c) Color (R.H.S.): Yellow Green 145C. d) Pollen color (R.H.S.): Yellow 11B. e) Texture/pubescence: Smooth. J. Pistils 1. Number 1 reduced. 2. Ovary size (L×W)—About 1.5 mm×2.0 mm, color — Yellow Green 150D, texture — minutely 4 lobed, pubescence none. 3. Stigma Shape oblong; color (R.H.S.) — Yellow Green 146B, Texture — smooth; pubescence none. 4. Style — size (L×W) — About 2 mm×1 mm; color White 155B, texture smooth, pubescence none.

*Fruit & seed*.—The cultivar is male plant, so no fruit or seed is produced.

Hardiness: Plants in the field in Watkinsville, GA have been cold hardy down to 6° F. with no foliar damage and have survived summer temperatures as high as 99° F.

Disease/pest resistance: To date, plants of the new *Ilex* have been observed to have notable resistance to spider mites (*Tetranychus*) as compared to other *Ilex* cultivars grown under similar conditions.

What is claimed is:

1. A new and distinct cultivar of the *Ilex* plant named 'RutHol8' as illustrated and described herein.

* * * * *